United States Patent [19]

Ryohei et al.

[11] Patent Number: 4,692,330

[45] Date of Patent: Sep. 8, 1987

[54] PROCESS FOR ACCELERATING ANTIGEN-ANTIBODY REACTION

[75] Inventors: Yamamoto Ryohei; Kimura Shigeki, both of Aichi; Matsuura Akira, Kasugai, all of Japan

[73] Assignee: Amano Pharmaceutical Co., Ltd., Japan

[21] Appl. No.: 778,558

[22] Filed: Sep. 20, 1985

[51] Int. Cl.$^4$ .................. A61K 39/00; A61K 43/00; A61K 39/395

[52] U.S. Cl. .................................... 424/85; 530/402; 530/403; 435/7; 436/547

[58] Field of Search .................. 424/85; 530/402, 403; 435/7; 436/547

[56] References Cited

U.S. PATENT DOCUMENTS

| | | | |
|---|---|---|---|
| 4,350,683 | 9/1982 | Galfrè et al. | 424/85 |
| 4,364,932 | 12/1982 | Kung et al. | 424/85 |
| 4,485,177 | 11/1984 | Siedel et al. | 424/85 |
| 4,565,687 | 1/1986 | Khazaeli et al. | 424/1.1 |
| 4,572,800 | 2/1986 | Shimizu et al. | 514/2 |

Primary Examiner—John Kight
Assistant Examiner—Nathan M. Nutter
Attorney, Agent, or Firm—McGlew and Tuttle

[57] ABSTRACT

A process for accelerating an antigen-antibody reaction by adding accelerator(s) such as dextran or alkylene glycol(s) and/or a polyalkylene glycol(s) to the reaction liquor of the antigen-antibody reaction.

24 Claims, 2 Drawing Figures

PROCESS FOR ACCELERATING ANTIGEN-ANTIBODY REACTION

DESCRIPTION

2. Technical Field

This invention relates to a process for accelerating an antigen-antibody reaction in vitro. More particularly, it relates to a process for accelerating an antigen-antibody reaction which comprises adding accelerator(s) such as dextran or alkylene glycol(s) and/or polyalkylene glycol(s) to the reaction mixture of said antigen-antibody reaction.

This process for accelerating an antigen-antibody reaction may be useful both in detecting substances present in biological fluids by an antigen-antibody reaction, and also useful in isolating and purifying substances by an antigen-antibody reaction.

2. Background Art

Antigen-antibody reactions have been widely employed in specifically determining trace substances present in biological fluids by immunoassay methods. They are further available in isolating and/or purifying trace components present in biological fluids by various techniques including affinity chromatography. For example, Miyai et al. have reported purification of antibody to thyrotropin by affinity chromatography through an antigen-antibody reaction and immunoassay for thyrotropin with the use of the antibody thus purified [cf. Clinical Chemistry, vol. 27 (8), 1981]. M. Kuroki et al. have reported purification of carcinoembryonic antigen (CEA)-related antigen by affinity chromatography by an antigen-antibody reaction [cf. Cancer Research, vol. 41, 713–720 (1981)]. However, antigen-antibody reactions have a disadvantage that they require several to several tens of hours for completion (cf. European Pat. No. 0051183, p. 2, lines 6 to 9). To illustrate this disadvantage more particularly, some immunoassay processes will be given by way of example. According to a report by K. Kato et al., determination of insulin by an enzyme immunoassay required two hours for the primary reaction at 30° C. and one night for the secondary reaction at 4° C. [cf. Clinica Chimica Acta, vol. 120, 261–265 (1980) and FEBS LETTERS vol. 99 (1), 172–174 (1979)]. In addition, Y. Tsung et al. have reported that determination of α-fetoprotein by radioimmunoassay requires three hours [cf. Journal of Immunological Methods, vol. 39, 363–368 (1980)] while Lynn R. Witherspoon et al. have reported that determination of triiodothyronine and thyrotropin requires two hours at room temperature or 37° C. [cf. Clinical Chemistry, vol. 31 (3), 415–419 (1985)].

Thus an antigen-antibody reaction would require generally several hours and sometimes one night or longer for completion Recent advances in immunology have made it possible to determine some substances in a relatively short period and, for instance, Charles A. Schiffer et al. have reported immunoassay processes requiring 45 to 60 min. [cf. Blood, vol. 61 (2), 311–317 (1983)]. However, antigen-antibody reactions still require a longer period than with other biochemical or chemical analyses so that it has been desired to accelerate the above reactions.

Accordingly it is an essential point how to accelerate or promote an antigen-antibody reaction in detecting a substance present in an organism by the antigen-antibody reaction or in isolating and purifying a substance by various techiques such as affinity chromatography.

4. Disclosure of the Invention

Under these circumstances, we have studied to solve the problem of antigen-antibody reactions requiring a long period for completion. That is, since addition of some substances capable of accelerating an antigen-antibody reaction to the reaction mixture might increase the efficiency of the antigen-antibody reaction, we have sought available accelerators. As a result, we have unexpectedly found that dextran or alkylene glycol(s) and/or polyalkylene glycol(s) would be effective therefor.

Any commercially available dextran may be used as an accelerator of the present invention. The dextran preferably has a molecular weight of 100 to 1,000,000 by taking into consideration its viscosity when dissolved in the reaction mixture. A fraction of a particular molecular weight or a mixture of fractions of various molecular weights would exhibit similar effects. The effective concentration of the dextran in the reaction mixture is 0.1% or higher. The upper limit of the dextran concentration is not particularly determined although it is desirable that the dextran concentration dose not exceed 10% from the viewpoint of its viscosity.

The alkylene glycol or polyalkylene glycol used as another accelerator in the present invention is represented by the following general formula:

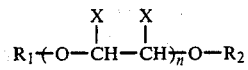

wherein n represents an integer of 1 or above and $R_1$, $R_2$, X and Y represent each a hydrogen atom or an alkyl group.

More particularly, ethylene glycol, polyethylene glycol, propylene glycol, polypropylene glycol and similar compounds are included therein. These alkylene glycols and/or polyalkylene glycols may be used alone. Alternately a mixture thereof may be employed. The effective concentration of the alkylene glycol(s) and/or polyalkylene glycol(s) in the reaction mixture is 0.5% or higher. The upper limit thereof is preferably not exceeding 10% by taking into consideration the effects of raising the viscosity of the reaction mixture and insolubilizing the antigen, antibody or other constituents therein.

Antigens, modified antigens, antibodies and modified antibodies, which are reactants in the antigen-antibody reaction accelerated by adding dextran or alkylene glycol(s) and/or polyalkylene glycol(s), include the following materials for example. The antigens include unmodified antigens, native antigens or fractions of a binding site to a corresponding antibody. The modified antigens include antigens labeled with a detectable functional group such as a radioisotope, a fluorescent material, a pigment, an enzyme or a metal or antigens immobilized on various insoluble carriers. The antibodies include those to various antigens, those to antibodies (i.e. so-called secondary or tertiary antibodies) or fractions of a binding site to an antigen therefor, such as F(ab')$_2$, Fab' and Fab. The modified antibodies include antibodies labeled with a detectable functional group as described above or those insolubilized on various insoluble carriers.

Immunochemical reactions, to which the present invention may be applied, include determination of trace substances, pharmaceuticals and antibodies by various methods with taking advantage of an antigen-antibody reaction and purification of substances by an antigen-antibody reaction.

Acceleration of an antigen-antibody reaction in vitro in the methods as described above shortens the determination period, which results in rapid clinical diagnoses. In addition, effective isolation and purification of substances originating from organisms such as trace hormones by an immulogical method may be remarkably useful in medical and biochemical fields.

5. BRIEF DESCRIPTION OF THE DRAWINGS

6. BEST MODES FOR CARRYING OUT THE INVENTION

Figure 1:
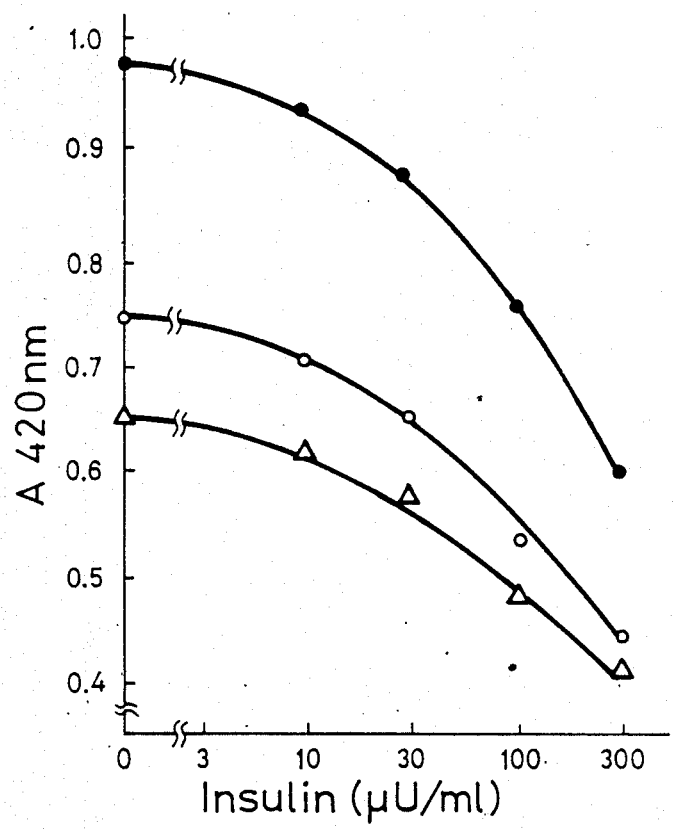
FIG. 1 shows calibration curves for the insulin determination in Example 3, wherein Δ represents a case where no dextran is added, ○ represents a case where 1% of Dextran T-500 is added and ● represents a case where 3% of Dextran T-500 is added.

The process for accelerating an antigen-antibody reaction of the present invention may be carried out as follows.

(i) A process which comprises adding accelerator(s) during an antigen-antibody reaction between a carrier whereon an antigen (antibody) is immobilized and an antibody (antigen) to thereby accelerate said antigen-antibody reaction.

This process is effective in isolating and purifying a substance.

(ii) A process which comprises adding accelerator(s) to the reaction mixture during determination of an antibody or an antigen by a reaction between a carrier whereon an antigen (antibody) is immobilized and a labeled antibody or labeled antigen as well as antigen or antibody to thereby accelerate said reaction.

This process is effective in detecting a trace substance in a biological fluid by a so-called immunoassay.

(iii) A process which comprises adding accelerator(s) to the reaction liquor during a reaction among an antigen to be assayed, an antibody (I) to said antigen and a labeled antibody (II) to form an antibody (I)-antigen-labeled antibody (II) complex to thereby accelerate the reaction and another reaction between the complex thus formed and the insolubilized second antibody to the antibody (I).

This process is effective in immunologically assaying a substance in a biological fluid.

We have devised the following two methods for the determination of the accelerating effect of the process of the present invention on an antigen-antibody reaction.

(1) A method which comprises comparing the amounts of immunoproducts formed within a particular period in the presence and absence of accelerator(s) to thereby determine the accelerating effect in the former case.

(2) A method which comprises drawing calibration curves of immunoproducts formed in the presence and absence of accelerator(s) and determining the accelerating effect in the former case by comparing changes in absorbance in both cases.

Accelerating effects of the process of the present invention on antigen-antibody reactions in the following examples were evaluated by either of the above determination methods.

The process according to the present invention is more specifically illustrated by the following examples without however limiting it in any way.

EXAMPLE 1

Acclerating effect of addition of dextran on immunological reaction evaluated by immunoproduct-gain method (1) Preparation of insulin immobilized on Sepharose 1 mg of commercially available crystalline insulin originating from swine pancreas was immobilized on 20 ml of CNBr-activated Sepharose (mfd. by Pharmacia AB) in a conventional manner. Then it was packed into a column (0.1 ml) and subjected to the subsequent procedure.

(2) Preparation of enzyme-labeled anti-insulin antibody

Commercially available antibody to insulin originating from guinea pig was digested with pepsin and reduced with mercaptoethylamine to give an Fab' fragment. The SH residue of the Fab' fragment was linked to the SH residue of β-D-galactosidase obtained from *Escherichia coli* using N,N'-o-phenylenedimaleimide.

(3) Binding of enzyme-labeled anti-insulin antibody to column

The enzyme-labeled anti-insulin antibody was diluted with a phosphate buffer solution containing 0.1% of bovine serum albumin. 0.5 ml of this dilution was passed through the column of the insulin immobilized on Sepharose prepared in the above item (1). The enzyme-labeled anti-insulin antibody was simultaneously diluted with the same phosphate buffer solutions containing 3% of glucose, Dextran T-70 (mfd. by Pharmacia AB) and Dextran T-500 (mfd. by Pharmacia AB) respectively and each dilution was treated in the same manner as described above. After washing the column, an aqueous solution of o-nitrophenyl-β-D-galactoside (o-NPG), which is the substrate for the enzyme, was poured thereto to perform an enzymatic reaction. Then the column was washed and the amount of o-nitrophenol in the eluate from the column, which was the product of the enzymatic reaction, was determined by measuring the absorbance at 420 nm. Table 1 shows the result. As shown in Table 1, the absorbance is directly proportional to the amount of the enzyme-labeled anti-insulin antibody bound to the column. Since the flow rate was constant, the addition of 3% of the dextran increased the amount of the enzyme-labeled anti-insulin antibody bound to the column approximately 1.6 times as much as that of the control case, showing a significant accelerating effect on the antigen-antibody reaction.

TABLE 1

| Additive | A 420 nm (amount of enzyme-labeled anti-insulin antibody bound to column) |
|---|---|
| none | 0.433 |
| glucose | 0.460 |
| Dextran T-70 | 0.637 |
| Dextran T-500 | 0.701 |

EXAMPLE 2

Accelerating effect of addition of alkylene glycol or polyalkylene glycol or immunological reaction evaluated by immunoproduct-gain method The procedure of Example 1 was followed except that the dextran was substituted by 1.5% of ethylene glycol, propylene glycol and polyethylene glycol having a molecular weight of approximately 6,000, respectively. Table 2 shows the result. As shown in Table 2, the addition of the polyalkylene glycols significantly accelerated the binding of the enzyme-labeled anti-insulin antibody to the column. For example, the polyethylene glycol increased the amount of the enzyme-labeled anti-insulin antibody bound to the column approximately 1.34 times as much as that of the control case, showing a significant accelerating effect on the antigen-antibody reaction.

TABLE 2

| Additive | A 420 nm (amount of enzyme-labeled anti-insulin antibody bound to column) |
| --- | --- |
| none | 0.521 |
| propylene glycol | 0.625 |
| ethylene glycol | 0.640 |
| polyethylene glycol | 0.700 |

EXAMPLE 3

Accelerating effect of addition of dextran on immunological reaction evaluated by insulin calibration curve method The same enzyme-labeled anti-insulin antibody and the same insulin immobilized on Sepharose as used in Example 1 were employed. 100 μl portions of various insulin solutions (0, 10, 30, 100 and 300 μU/ml) and 0.5 ml of the solution of the enzyme-labeled anti-insulin antibody were allowed to react at 30° C. for one hour. This reaction mixture was applied to a column of the insulin immobilized on Sepharose. Then the column was washed and filled with an o-NPG solution to thereby carry out an enzymatic reaction at 30° C. for one hour. Simultaneously solutions of the enzyme-labeled anti-insulin antibody containing 1% or 3% of Dextran T-500, respectively, were subjected to the same treatment. After the completion of the enzymatic reaction, the column was washed with a sodium carbonate solution and the absorbance at 420 nm of the washing liquor was measured to thereby obtain calibration curves shown in FIG. 1. These calibration curves clearly show that the sample containing no dextran exhibits a smaller change in the absorbance at 420 nm then those containing dextran when determined in the same period. Therefore it is obvious that calculation of the insulin concentration from the calibration curve of the former sample might result in some errors caused by scatter. For example, when a serum containing approximately 30 μU/ml of insulin was determined in the absence of dextran and in the presence of 3% of the same, the CV (%) of the former case was 34% while that of the latter case was 9.5%. A reaction period at least twice as long as that of the case where 3% of Dextran T-500 was added was required to obtain a similarly practical absorbance in the absence of the dextran. That is to say, the addition of the dextran shortened the antigen-antibody reaction period to ½ of that of conventional methods.

EXAMPLE 4

Figure 2:
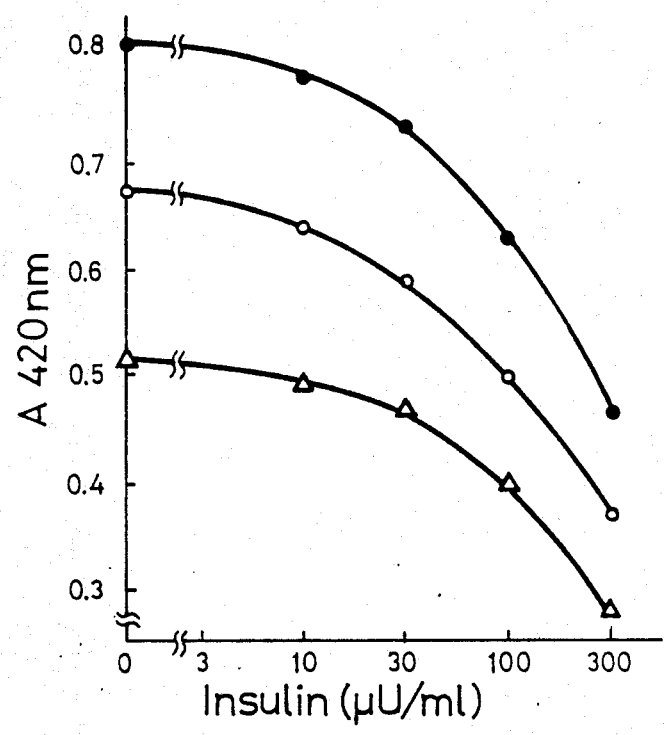
FIG. 2 shows calibration curves for the insulin determination in Example 4, wherein Δ represents a case where neither alkylene glycols nor polyalkylene glycols are added, ○ represents a case where 2% of ethylene glycol is added and ● represents a case where 2% of polyethylene glycol is added.

Accelerating effect of addition of ethylene glycol or polyethylene glycol on immunological reaction evaluated by insulin calibration curve method The procedure of Example 3 was followed except that the Dextran T-500 was substituted by 2% of ethylene glycol or 2% of polyethylene glycol. FIG. 2 shows the result. The calibration curves shown in FIG. 2 clearly indicate that the sample containing neither ethylene glycol nor polyethylene glycol exhibits a smaller change in the absorbance at 420 nm than those containing ethylene glycol or polyethylene glycol when determined within the same period. Therefore it is obvious that calculation of the insulin concentration from the calibration curve of the former sample might result in some errors caused by scatter. For example, a serum containing 30 μU/ml of insulin was determined in the absence of polyethylene glycol and in the presence of 2% of the same. The CV (%) of the former case was 30% while that of the latter case was 11%. A reaction period at least twice as long as that of the case where 2% of ethylene glycol was added was required to obtain a similarly practical absorbance in the absence of polyethylene glycol. That is, the addition of the ethylene glycol or polyethylene glycol shortened the antigen-antibody reaction period to ½ of that of conventional methods.

EXAMPLE 5

Accelerating effect of addition of dextran on immunological reaction evaluated by immunoproduct-gain method (1) Preparation of enzyme-labeled anti-enolase antibody The procedure of Example 1-(2) was followed except that anti-enolase antibody originating from rabbit was used.

(2) Preparation of anti-enolase monoclonal antibody

Enolase was injected into mice and those producing the antibody were employed. Antibody-producing hybridomas were prepared from spleen from these mice and myeloma cells. The hybridomas thus obtained were cultured and anti-enolase monoclonal antibody (hereinafter referred to MCAb) was isolated from the medium in a conventional manner.

(3) Preparation of anti-mouse IgG antibody (second antibody) immobilized on Sepharose The procedure of Example 1-(1) was followed.

(4) Formation of enolase/antibody complex

An enolase solution and a MCAb solution were mixed and the mixture was allowed to react for 30 min. Simultaneously the same mixture except containing 1% of Dextran T-500 was subjected to the same reaction. In order to determine the MCAb/enolase complex formed by the above reaction, the enzyme-labeled anti-enolase antibody was added to the reaction mixture to form an MCAb/enolase/enzyme-labeled anti-enolase antibody complex which was subsequently applied to a column of the second antibody immobilized on Sepharose to thereby carry out the enzyme reaction in the same manner as described in Example 1. Table 3 shows the result obtained with varying the amount of the enolase. As shown in Table 3, the amount of the MCab/enolase complex formed in the presence of dextran within a particular period (i.e. 30 min.) is 1.49 to 1.60 times as much as that formed in the absence of dextran, thus showing a significant accelerating effect on the antigen-antibody reaction.

TABLE 3

| Amount of enolase (ng/tube) | Absorbance at 420 nm | |
| --- | --- | --- |
| | no dextran added | dextran added |
| 0.75 | 0.210 | 0.320 |
| 2.25 | 0.450 | 0.720 |
| 6.75 | 1.08 | 1.61 |

EXAMPLE 6

Accelerating effect of addition of polyethylene glycol on immunological reaction evaluated by immunoproduct-gain method The procedure of Example 5 was followed except that 1% of Dextran T-500 was substituted by 1.5% of polyethylene glycol. Table 4 shows the result. As shown in Table 4, the amount of the MCAb/enolase complex formed in the presence of 1.5% of polyethylene glycol within a particular period (i.e. 30 min.) was 1.39 to 1.45 times as much as that formed in the absence of polyethylene glycol, thus showing a significant accelerating effect on the antigen-antibody reaction.

TABLE 4

| Amount of enolase (ng/tube) | Absorbance at 420 nm | |
| --- | --- | --- |
| | no polyethylene glycol added | polyethylene glycol added |
| 0.75 | 0.280 | 0.390 |
| 2.25 | 0.570 | 0.800 |
| 6.75 | 1.10 | 1.60 |

We claim:

1. Process for accelerating an antigen-antibody reaction which comprises adding dextran to the reaction mixture of an immunochemical reaction in vitro of at least one of an antigen and a modified antigen, with at least one of an antibody therefor and a modified antibody therefor, to thereby accelerate the and said modified antibody each independently being modified by being immobilized on an insoluble carrier or by being labeled with a detectable substance.

2. Process of claim 1 wherein the reaction mixture comprises an antigen and a modified antibody therefor which is immobilized on an insoluble carrier.

3. Process of claim 1 wherein the reaction mixture comprises an antibody and a modified antigen therefor which is immobilized on an insoluble carrier.

4. Process of claim 1 wherein the reaction mixture comprises an antigen, a modified antigen which is labeled with a detectable substance, and antibodies therefor.

5. Process of claim 1 wherein the reaction mixture comprises an antigen, a modified antigen which is labeled with a detectable substance and modified antibodies therefor which are immobilized on an insoluble carrier.

6. Process of claim 1 wherein the reaction mixture comprises an antigen and a modified antibody therefor which is labeled with a detectable substance.

7. Process of claim 1 wherein the reaction mixture comprises an antibody and a modified antigen therefor which is labeled with a detectable substance.

8. Process of claim 1 wherein the reaction mixture comprises a complex of a modified antigen which is labelled with a detectable substance and an antibody, and a modified antigen for said antibody which modified antigen is immobilized on an insoluble carrier.

9. Process of claim 1 wherein the reaction mixture comprises a complex of a modified antibody which is labelled with a detectable substance and an antigen, and a modified antibody for said antigen which modified antibody is immobilized on an insoluble carrier.

10. Process of claim 1 wherein the reaction mixture comprises a complex of an antibody (I), an antigen and a modified antibody (II) which is labelled with a detectable substance, and another modified antibody (III) which is an antibody to said antibody (I) and which is immobilized on an insoluble carrier.

11. Process of claim 1 wherein the reaction mixture comprises a complex of an antibody (I) and a modified antigen which is labelled with a detectable substance, and a modified antibody (II) which is an antibody to said antibody (I) and which is immobilized on an insoluble carrier.

12. Process of claim 1 wherein the detectable substance is an enzyme.

13. Process for accelerating an antigen-antibody reaction which comprises adding dextran to the reaction mixture of an immunochemical reaction in vitro of an antigen containing material and a corresponding antibody containing material, to thereby accelerate the corresponding antigen-antibody reaction.

14. Process of claim 13 wherein the antigen containing material comprises at least one of an antigen, a labelled antigen which is labelled with a detectable substance, and an immobilized antigen which is immobilized on an insoluble carrier, and the antibody containing material comprises at least one of an antibody, a labelled antibody which is labelled with a detectable substance, and an immobilized antibody which is immobilized on an insoluble carrier.

15. Process of claim 14 wherein the reaction mixture comprises an antigen and an immobilized or labelled antibody therefor.

16. Process of claim 14 wherein the reaction mixture comprises an antibody an and immobilized or labelled antigen therefor.

17. Process of claim 14 wherein the reaction mixture comprises an antigen, a labelled antigen, and antibodies or immobilized antibodies therefor.

18. Process of claim 14 wherein the reaction mixture comprises a complex of a labelled antigen which is labelled with an enzyme and an antibody, and an immobilized antigen for said antibody.

19. Process of claim 14 wherein the reaction mixture comprises a complex of a labelled antibody which is labelled with an enzyme and an antigen, and an immobilized antibody for said antigen.

20. Process of claim 14 wherein the reaction mixture comprises a complex of an antibody (I), and antigen and a labelled antibody (II) which is labelled with an enzyme, and an immobilized antibody (III) which is an antibody to said antibody (I).

21. Process of claim 14 wherein the reaction mixture comprises a complex of an antibody (I) and a labelled antigen which is labelled with an enzyme, and an immobilized antibody (II) which is an antibody to said antibody (I).

22. Process of claim 15 wherein the labelled antibody is labelled with an enzyme.

23. Process of claim 16 wherein the labelled antigen is labelled with an enzyme.

24. Process of claim 17 wherein the labelled antigen is labelled with an enzyme.

* * * * *